United States Patent
Jirman et al.

(10) Patent No.: US 8,034,807 B2
(45) Date of Patent: Oct. 11, 2011

(54) SALTS OF BAZEDOXIFENE

(75) Inventors: Josef Jirman, Praha (CZ); Jindrich Richter, Pardubice (CZ)

(73) Assignee: Zentiva k.s., Praha (CZ)

( * ) Notice: Subject to any disclaimer, the term of this patent is extended or adjusted under 35 U.S.C. 154(b) by 0 days.

(21) Appl. No.: 12/670,574

(22) PCT Filed: Jul. 24, 2008

(86) PCT No.: PCT/CZ2008/000089
§ 371 (c)(1),
(2), (4) Date: May 24, 2010

(87) PCT Pub. No.: WO2009/012734
PCT Pub. Date: Jan. 29, 2009

(65) Prior Publication Data
US 2010/0240888 A1  Sep. 23, 2010

(30) Foreign Application Priority Data
Jul. 25, 2007 (CZ) .................................. 2007-500

(51) Int. Cl.
*A61K 31/404* (2006.01)
*A61P 5/30* (2006.01)
*C07D 209/12* (2006.01)

(52) U.S. Cl. .................. 514/217.08; 540/602

(58) Field of Classification Search ............. 514/217.08; 540/602
See application file for complete search history.

(56) References Cited

U.S. PATENT DOCUMENTS
| | | |
|---|---|---|
| 5,998,402 A | 12/1999 | Miller et al. |
| 6,479,535 B1 | 11/2002 | Pickar et al. |
| 2005/0227964 A1 | 10/2005 | Fawzi et al. |
| 2005/0227965 A1 | 10/2005 | Demerson et al. |
| 2005/0227966 A1 | 10/2005 | Shah et al. |

FOREIGN PATENT DOCUMENTS
WO   WO 2006/104791   10/2006

OTHER PUBLICATIONS
International Search Report of international Patent Application No. PCT/CZ2002/000089, Date of Mailing: Jun. 17, 2009.
Chris P. Miller, Bazedoxifene Acetate, Selective Estrogen Receptor Modulator Treatment and Prevention of Osteoporosis, Drugs of the Future 2002, 117-121, 27(2).
Chris P. Miller, Design, Synthesis, and Preclinical Characterization of Novel, Highly Selective Indole Estrogens, Journal of Medical Chemistry, 2001, 1654-1657, 44.

*Primary Examiner* — Brenda Coleman
(74) *Attorney, Agent, or Firm* — Pearl Cohen Zedek Latzer, LLP

(57) ABSTRACT

The invention deals with new crystalline salts of bazedoxifene, by means of which a high API quality can be achieved in a high yield.

14 Claims, 5 Drawing Sheets

SALTS OF BAZEDOXIFENE

CROSS-REFERENCE TO RELATED APPLICATIONS

This application is a National Phase Application of PCT International Application No. PCT/CZ2008/000089, International Filing Date Jul. 24, 2008, entitled "New Salts of Bazedoxifene", published on Jan. 29, 2009 as International Publication Number WO 2009/012734 which claims priority of Czech Republic PV 2007-500 Patent Application filed on Jul. 25, 2007, both of which are incorporated herein by reference in their entirety.

TECHNICAL FIELD

The invention deals with new crystalline salts of the selective estrogen receptor modulator 1-[4-(2-azepan-1-yl-ethoxy)benzyl]-2-(4-hydroxyfenyl)-3-methyl-1H-indol-5-ol with polycarboxylic acids, in particular the salts with dicarboxylic and tricarboxylic acids and especially the salts with the proportion of constituents of 2:1.

BACKGROUND ART

Bazedoxifene (1-[4-(2-azepan-1-yl-ethoxy)benzyl]-2-(4-hydroxyfenyl)-3-methyl-1H-indol-5-ol) of formula 1:

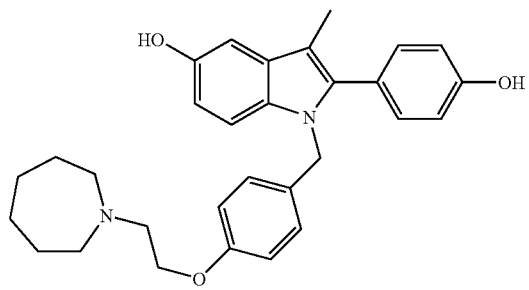

(1)

belongs to selective estrogen receptor modulators (SERMs). A more detailed description of its biological activity can be found e.g. in Drugs of the Future, 2002, 27(2), 117-121.
The preparation of bazedoxifene and its acetate was published in the U.S. Pat. Nos. 5,998,402 and 6,479,535. The preparation of bazedoxifene was also published in J. Med. Chem. 2001, 44, 1654-1657. US 2005/0227965 A1 compares two crystalline polymorphs of bazedoxifene acetate. US 2005/0227964 A1 discloses bazedoxifene ascorbate and its use.

Use of a substance for pharmaceutical purposes places high demands on the substance quality. The most efficient purification operation is crystallization. In the case of substances that cannot crystallize it is very difficult to achieve internationally appreciated quality criteria defined by the ICH instructions. In addition, amorphous forms of substances are more susceptible to decomposition, in particular hydrolysis or oxidation, which is caused by their large surface. According to well-known and verified information bazedoxifene and its hitherto known forms can be classified among such substances that are difficult to purify and prone to decomposition.

Bazedoxifene as well as bazedoxifene ascorbate are non-crystalline forms that can be obtained by concentrating the solution until dry. Due to this, however, all undesired, non-volatile substances coming from the synthesis or decomposition of API remain in the resulting substance. This is mainly the case of 2-(4-hydroxyphenyl)-3-methyl-1H-indol-5-ol of formula 2 and 1-[4-(2-azepan-1-yl-ethoxy)benzyl]-5-benzyloxy-2-(4-hydroxyphenyl)-3-methyl-1H-indole of formula 3, coming from the synthesis, and 1-(4-hydroxybenzyl)-2-(4-hydroxyphenyl)-3-methyl-1H-indol-5-ol of formula 4 and 1-[4-(2-azepan-1-yl-ethoxy)benzyl]-2-(4-hydroxyphenyl)-3-methyl-1H-indol-5-ol N-oxide of formula 5, generated by decomposition of bazedoxifene.

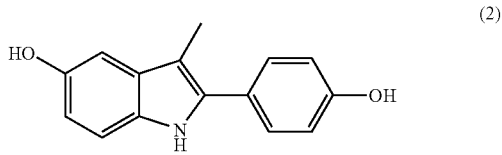

(2)

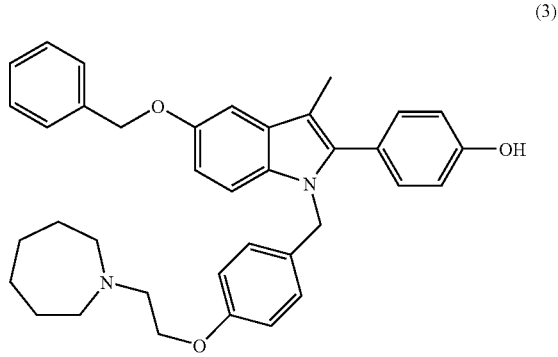

(3)

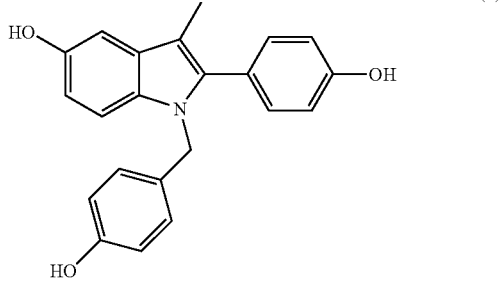

(4)

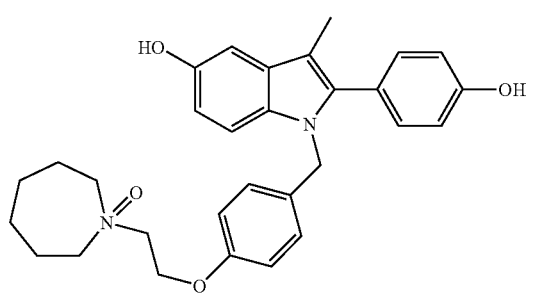

(5)

The allegedly crystalline acetate does not solve the problem of quality. The presence of even small quantities of the above mentioned or other impurities precludes crystallization of bazedoxifene acetate prepared in accordance with the patent documents U.S. Pat. Nos. 5,998,402; 6,479,535 or US 2005/0227965. The acetate can be successfully obtained in the amorphous form by a modified procedure with yields of about 40%. The acetate is subject to decomposition reactions producing undesired impurities, especially oxidation that produces the undesired substance of formula 5. To suppress this decomposition process the addition of ascorbic acid as an antioxidant is commonly used. Therefore, a more suitable form of bazedoxifene has been looked for that could be easily prepared in high yields and in particular in the quality corresponding to API and would not be susceptible to undesired decompositions at the same time.

DISCLOSURE OF INVENTION

The invention relates to new stable crystalline salts of 1-[4-(2-azepan-1-yl-ethoxy)benzyl]-2-(4-hydroxyphenyl)-3-methyl-1H-indol-5-ol (bazedoxifene) with acids containing two and more carboxylic groups and to a method of their preparation, characterized by the reaction of 1-[4-(2-azepan-1-yl-ethoxy)benzyl]-2-(4-hydroxyphenyl)-3-methyl-1H-indol-5-ol of formula 1 with a polycarboxylic acid in a suitable solvent. The process used, in which a chemical purity of the product of 99.9% and higher, with the contents of individual impurities below 0.1%, can be easily achieved, is described by the equation in Scheme 1. Also, an economical method of production of these salts has been found that can be used in the production scale as well.

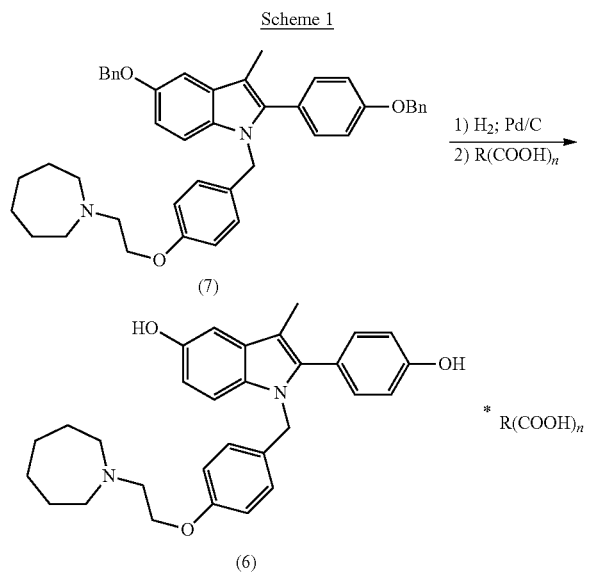

Scheme 1

From the chemical point of view our product is a salt that contains the constituent characterized by formula 1 and a polycarboxylic acid (R(COOH)$_n$ consisting of two or more carboxylic functional groups mutually connected with a covalent bond or a chain containing C and H, O, N, S or a halogen).

In the above mentioned formula the chain representing R may consist of residues of aliphatic or cyclic hydrocarbons with the length of C1 to C18. These hydrocarbon residues may be substituted with groups containing atoms of O, N, S or a halogen. They may also be substituted with NR$^1$R$^2$R$^3$ groups, wherein R$^1$, R$^2$ and R$^3$ are independently either hydrogen or a C1 to C5 hydrocarbon chain, O, OR$^1$, S, SR$^1$ or SO$_m$R$^1$, wherein m can have the values from 1 to 3, or a halogen, and n can have the values from 2 to 5. These hydrocarbon residues can further be substituted by OH groups.

The method of preparation of the substance of formula 6 is characterized by the use of a suitable solvent. The selection of the solvent depends on the solubilities of the starting substance and product and especially on the capability of the product to form a strong lattice in the given solvent. As the solvents, one can use C1-C5 alcohols (e.g. methanol, ethanol, 1-propanol, 2-propanol, butanols), esters of carboxylic acids (e.g. ethyl acetate), ethers (e.g. dioxan, tetrahydrofuran or diethyl ether), ketones (e.g. acetone or cyclobutanone), acetonitrile, their arbitrary mixtures and mixtures with water in any proportions. A preferable embodiment of the invention comprises using ethanol or its mixtures with water, with ethyl acetate or with toluene as the solvent in the proportions of 97.5:2.5 to 90:10. It has been proved that the selected procedure produces a crystalline salt of the compound of formula 6, which contains the compound of formula 1 and a polycarboxylic acid (e.g. fumaric, succinic, oxalic, maleic, tartaric or citric acid). An especially preferable form of the salt is in the proportion of 2:1.

A preferable form of the salt of the compound of formula 6 is the crystalline form, which is chemically stable, with a high chemical purity (above 99.5% according to HPLC), which can be prepared with high yields in a defined crystalline modification and which is characterized by a suitable size of particles for further processing. These conditions are fulfilled by the present crystalline forms of salts of bazedoxifene of formula 1 and polycarboxylic acids, in particular fumaric, oxalic, succinic, maleic, tartaric and citric acids.

The crystalline structure of said salts of formula 6 has been unambiguously characterized by the results of the following analytic methods: X-Ray Powder Diffraction (hereinafter XRPD only), melting point and Differential Scanning Calorimetry (hereinafter DSC only). The results of the analyses are presented in the examples and attached drawings.

It is especially beneficial to prepare the crystalline form of the salt of the compound of formula 6 of the present invention if an alcohol (C1-C5) or its mixtures with toluene, DMF or ethyl acetate in the proportions of 90:10 to 95:5 are used as the solvent. The process exclusively leads to a defined crystal modification (determined by means of DSC and XRPD) and a defined particle size and, in addition, this process manifests high quality and high yields, which are achieved in a reproducible manner. The above mentioned characteristics of the crystalline salt of the compound of formula 6 are very advantageous for its manufacture and pharmaceutical use.

The process used has repeatedly led, with yields of 90 to 95%, to the crystalline salt of fumaric acid with 1-[4-(2-azepan-1-yl-ethoxy)benzyl]-2-(4-hydroxyphenyl)-3-methyl-1H-indol-5-ol, characterized by a high quality (HPLC content >99.95%).

The obtained salt of fumaric acid with 1-[4-(2-azepan-1-yl-ethoxy)benzyl]-2-(4-hydroxyphenyl)-3-methyl-1H-indol-5-ol of formula 10 can be used in practice for the preparation of pharmaceutically useful compositions.

The process used has further repeatedly produced crystalline salts of succinic acid ((CH$_2$COOH)$_2$) (bazedoxifene succinate), propanedioic acid (CH$_2$(COOH)$_2$) (bazedoxifene malonate), oxalic acid ((COOH)$_2$) (bazedoxifene oxalate), maleic acid ((CHCOOH)$_2$) (bazedoxifene maleate), hydroxybutanoic acid (COOHCH$_2$CHOHCOOH), (bazedoxifene hydroxybutanoate), tartaric acid ((CHOHCOOH)$_2$) (bazedoxifene tartrate) and citric acid (C(COOH)(OH)(CH$_2$COOH)$_2$) (bazedoxifene citrate), which also show high yields, high stabilities and can be used for the production of pharmaceutically useful compositions in practice.

The obtained salts of polycarboxylic acids with 1-[4-(2-azepan-1-yl-ethoxy)benzyl]-2-(4-hydroxyphenyl)-3-methyl-1H-indol-5-ol of formula 6 can be used for the preparation of pharmaceutically useful compositions in practice.

In the process of looking for the most suitable salt of 1-[4-(2-azepan-1-yl-ethoxy)benzyl]-2-(4-hydroxyphenyl)-3-methyl-1H-indol-5-ol (bazedoxifene) the hitherto not described salt with formic acid (HCOOH) (bazedoxifene formate) has also been prepared, as well as a new polymorph of the salt with acetic acid (CH₃COOH) (bazedoxifene acetate), which can also be used in practice for the preparation of pharmaceutically useful compositions, even though their yields and qualities are lower as compared to the salts of polycarboxylic acids, which only confirms the advantageousness of use of the salts of bazedoxifene free base with polycarboxylic acids.

The object of the invention will be elucidated in a more detailed way in the following examples, which, however, do not have any impact on the scope of protection defined by the claims.

EXAMPLES

Example 1

Figure 1:
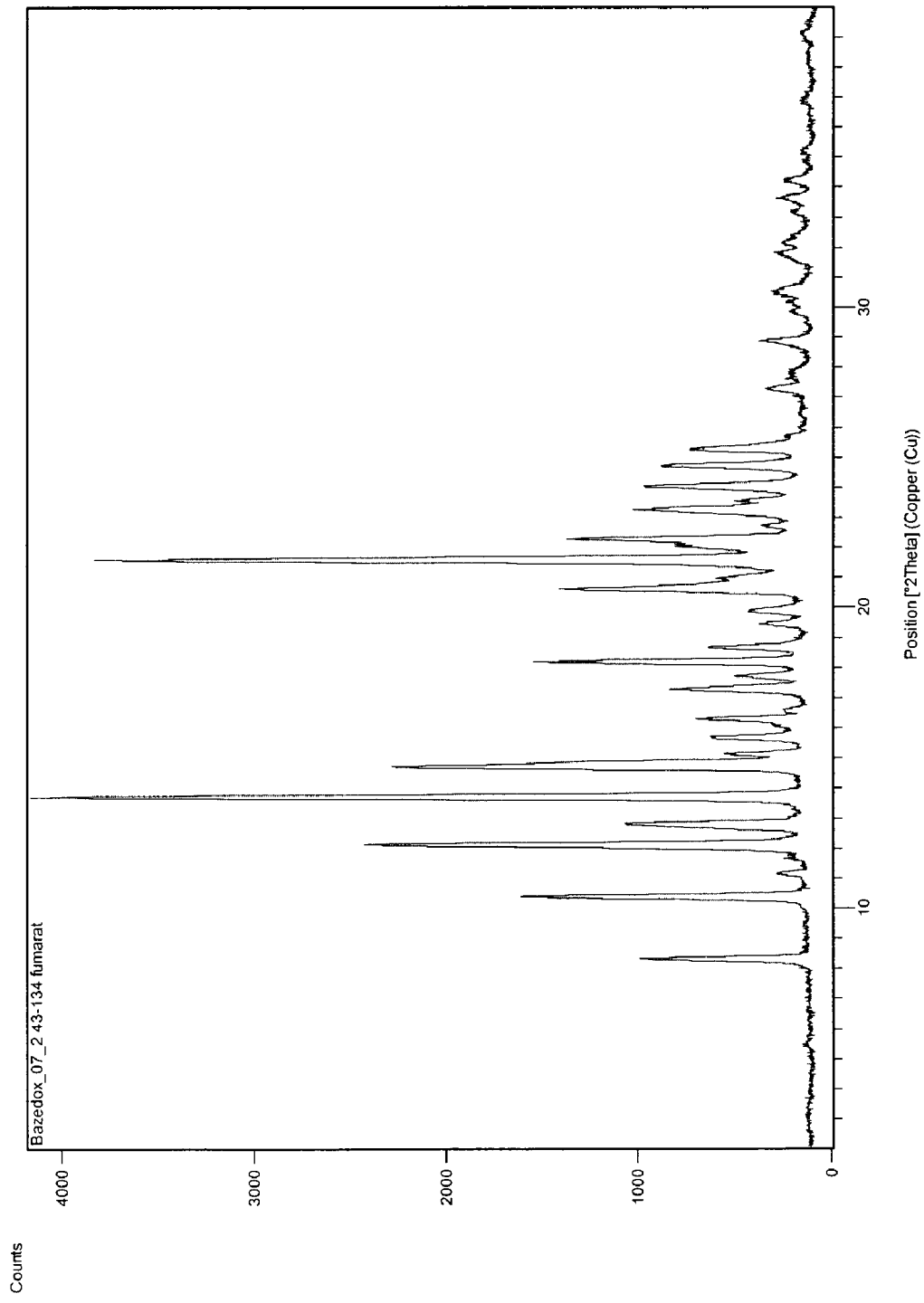
FIG. 1 shows the X-Ray Powder Diffraction of the crystalline salt of fumaric acid with bazedoxifene prepared according to Example 2 (bazedoxifene fumarate-polymorph A).
Figure 2:
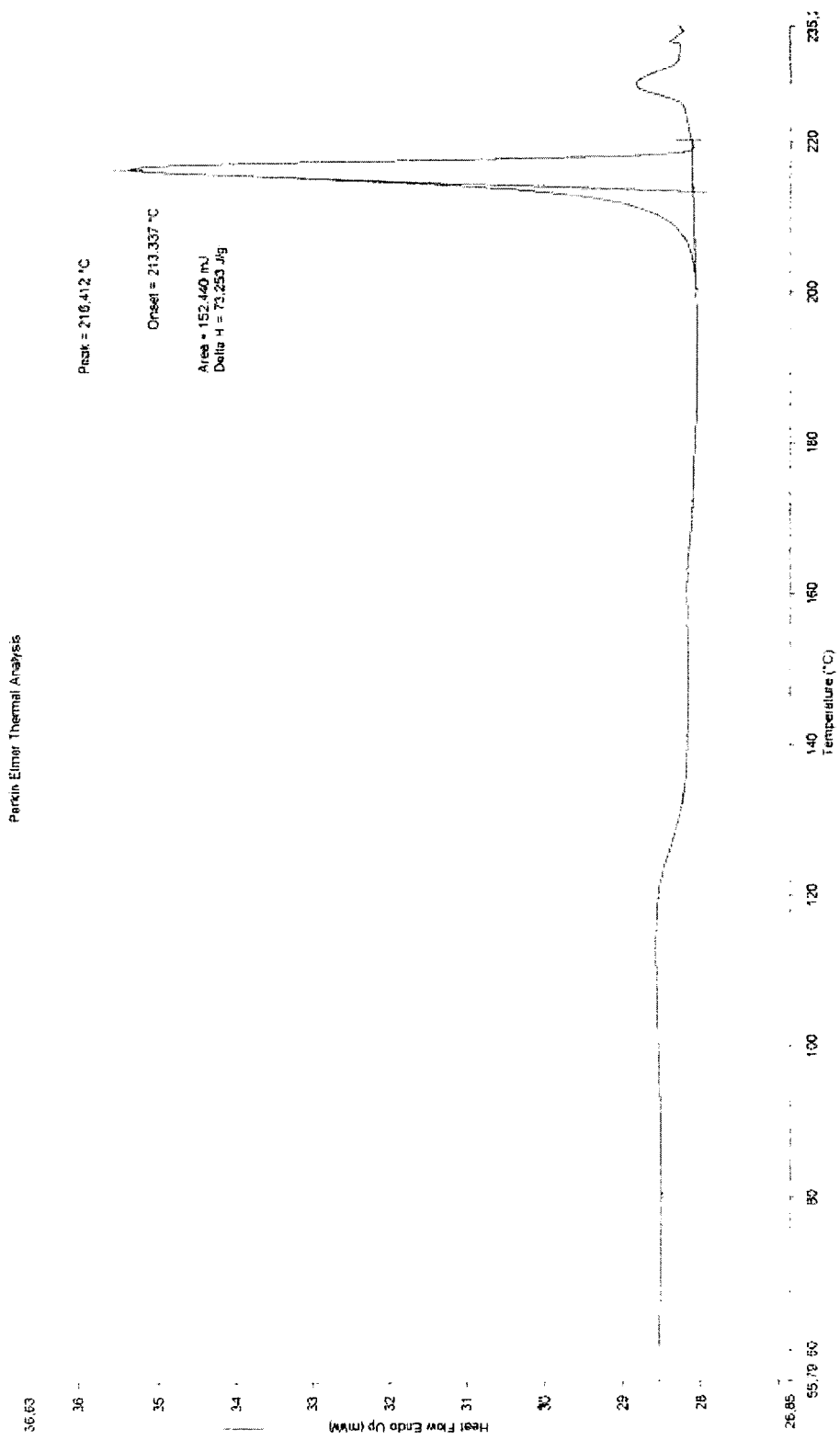
FIG. 2 shows the DSC curve of the crystalline salt of fumaric acid with bazedoxifene prepared according to Example 2 (bazedoxifene fumarate-polymorph A).
Figure 3:
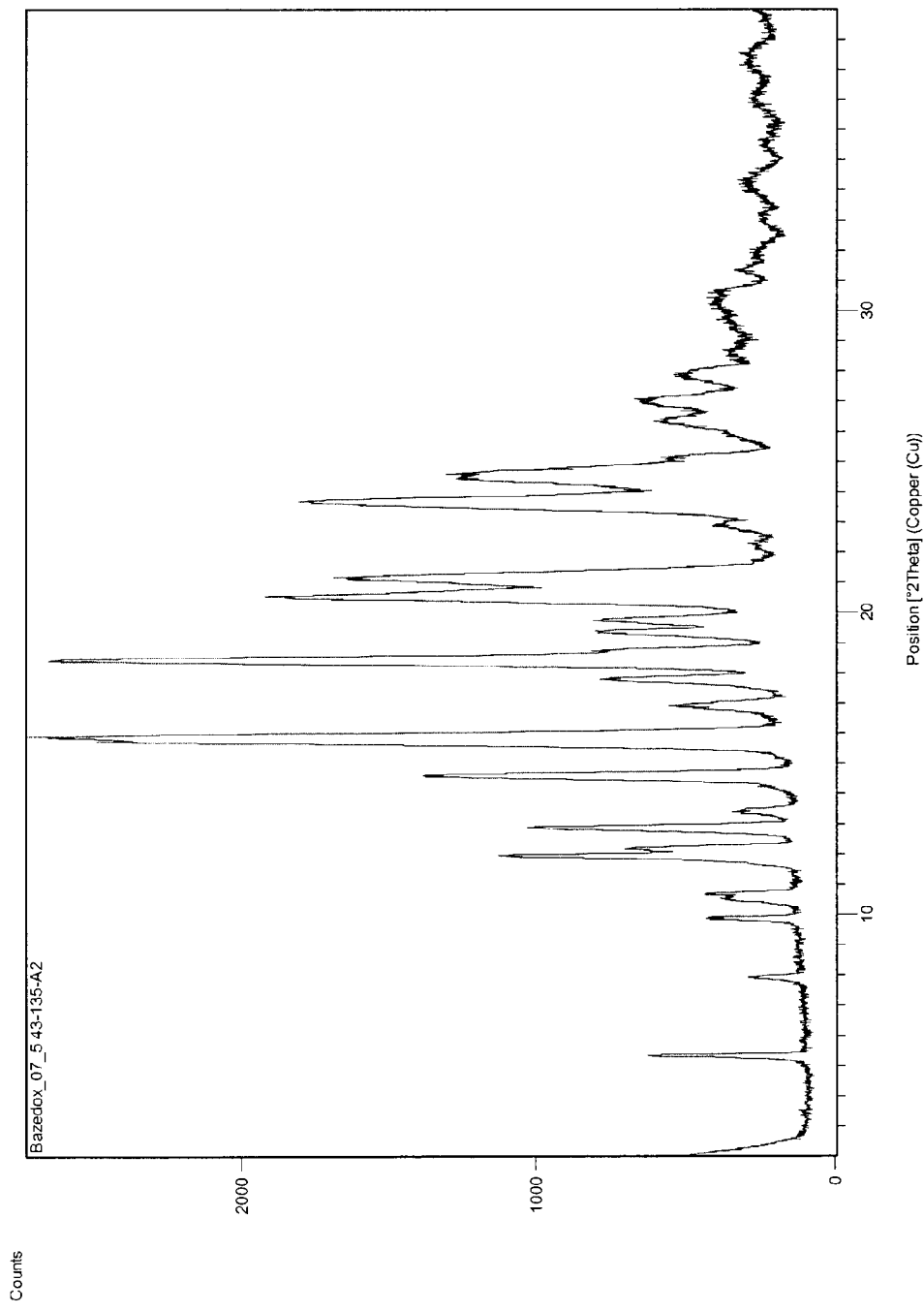
FIG. 3 shows the X-Ray Powder Diffraction of the crystalline salt of fumaric acid with bazedoxifene prepared according to Example 3 (bazedoxifene fumarate-polymorph B).
Figure 4:
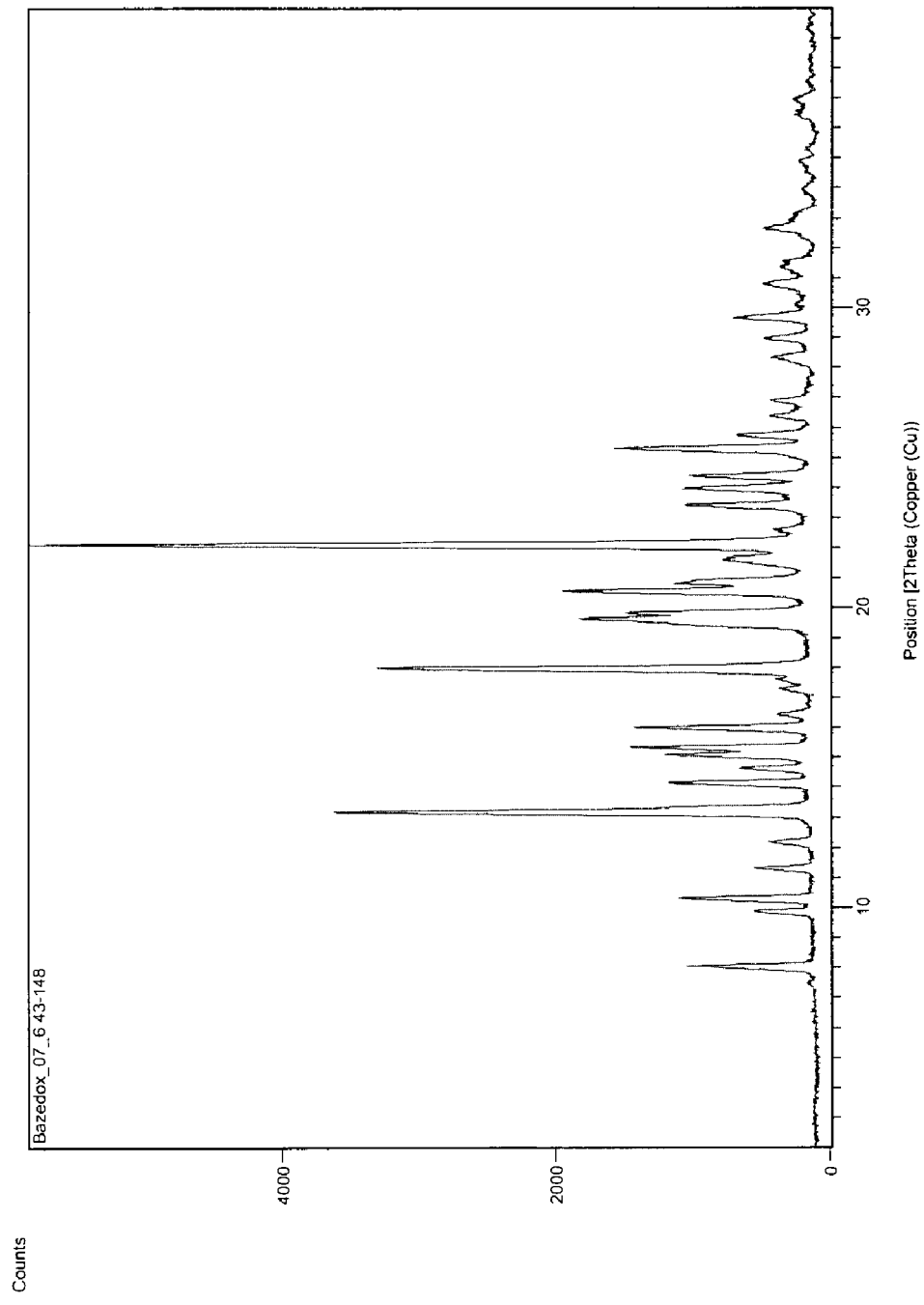
FIG. 4 shows the X-Ray Powder Diffraction of the crystalline salt of acetic acid with bazedoxifene polymorph C) prepared according to Example 10 (bazedoxifene acetate).
Figure 5:
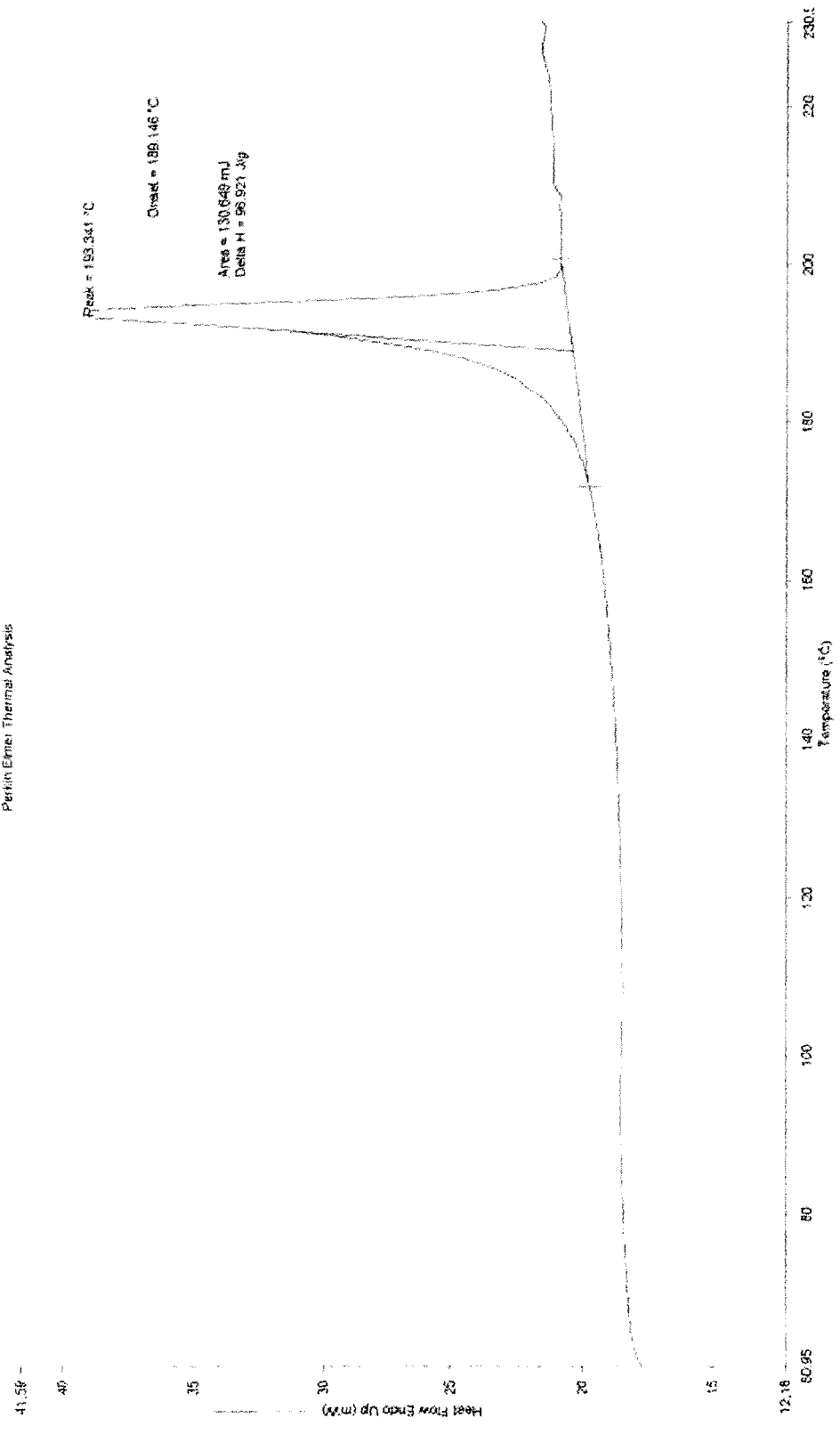
FIG. 5 shows the DSC curve of the crystalline salt of acetic acid with bazedoxifene polymorph C) prepared according to Example 10 (bazedoxifene acetate).

Preparation of 1-[4-(2-azepan-1-yl-ethoxy)benzyl]-2-(4-benzyloxyphenyl)-5-benzyloxy-3-methyl-1H-indole (benzylated bazedoxifene)

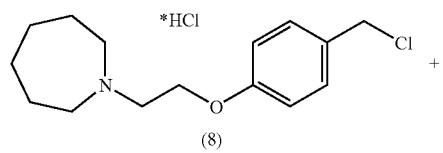

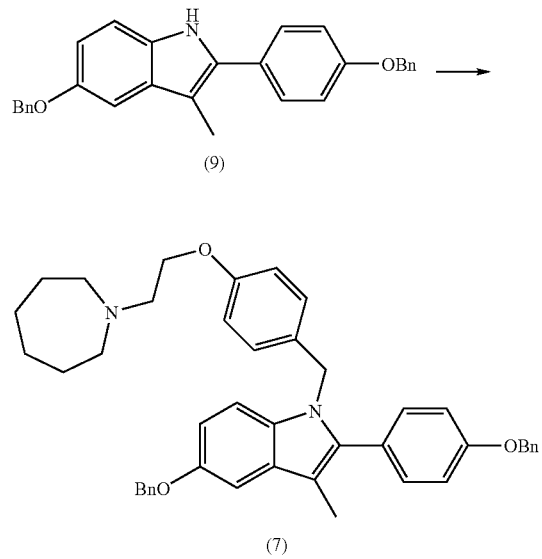

In an inert atmosphere NaH (2.7 g; 112 mmol) was suspended in DMF (80 ml). At 0-5° C. 5-benzyloxy-2-(4-benzyloxyphenyl)-3-methyl-1H-indole (11 g; 26 mmol) was added and the suspension was stirred for 30 minutes. Then a solution of 4-(2-azepan-1-yl-ethoxy)benzyl chloride (8 g; 26 mmol) in DMF (30 ml) was added dropwise within 1 hour. The cooling was shut down and the reaction mixture was stirred for another 2.5 hours. Then, water (1.2 ml) was carefully added dropwise to the reaction mixture and the reaction mixture was filtered through a thin layer of celite. Another 35 ml of water were added dropwise to the brightly yellow filtrate under intensive stirring.

The separated white product was filtered and washed with methanol. The yield of the crude product was 13.7 g (81%). The crude product was dissolved in 70 ml of ethyl acetate with a small quantity of activated charcoal and filtered while hot. 100 ml of methanol were added to the filtrate. The yield of crystallization was 80.5%. Melt. point=109-112° C. HPLC content 99.8%.

Example 2

Preparation of the Salt of 1-[4-(2-azepan-1-yl-ethoxy)benzyl]-2-(4-hydroxyphenyl)-3-methyl-1H-indol-5-ol with Fumaric Acid in the Proportion of 2/1 (bazedoxifene fumarate), polymorph A

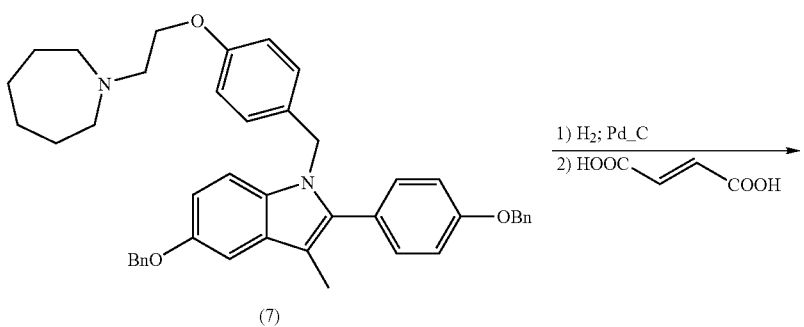

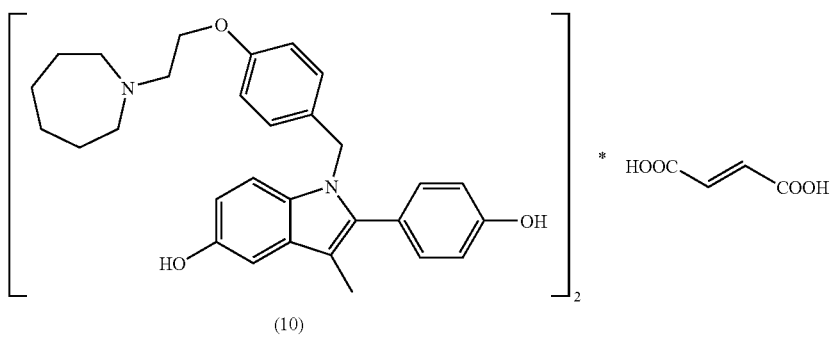

(10)

The starting compound, benzylated bazedoxifene of formula 7 (4 g; 6.15 mmol) was dissolved in ethanol (40 ml) and the catalyst, 2.34%-Pd/C (0.4 g), was added in an inert atmosphere. Then, the reaction mixture was stirred in the hydrogen atmosphere for 5 hours. The catalyst was filtered off through a celite layer in an inert atmosphere. The obtained clear, colourless filtrate was inoculated with bazedoxifene fumarate of formula 6 (0.1 g). Then, an ethanolic solution (10 ml) of fumaric acid (0.36 g, 3.075 mmol) was added to the solution dropwise within 30 minutes.

The separated white, crystalline product was filtered and dried in a nitrogen stream at 50° C. 3 g (93%) of the crystalline fumarate (polymorph A) were obtained with the HPLC purity of >99.95%. Melt. point=221-224° C.

Example 3

Preparation of the Salt of 1-[4-(2-azepan-1-yl-ethoxy)benzyl]-2-(4-hydroxyphenyl)-3-methyl-1H-indol-5-ol with Fumaric Acid in the Proportion of 2/1 (bazedoxifene fumarate), polymorph B

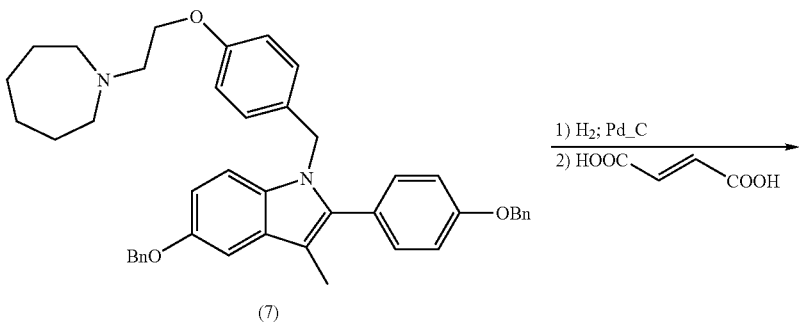

(7)

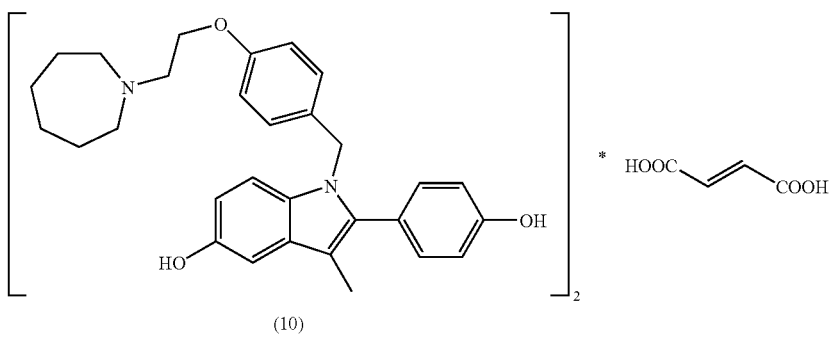

(10)

The starting compound, benzylated bazedoxifene of formula 7 (4 g; 6.15 mmol) was dissolved in an ethanol/ethyl acetate mixture (95:5) (40 ml) and the catalyst, 2.34%-Pd/C (0.4 g) was added in an inert atmosphere. Then, the reaction mixture was stirred in the hydrogen atmosphere for 5 hours. The catalyst was filtered off through a celite layer in an inert atmosphere. The obtained clear, colourless filtrate was inoculated with bazedoxifene fumarate of formula 6 (0.1 g). Then, an ethanolic solution (10 ml) of fumaric acid (0.36 g, 3.075 mmol) was added to the solution dropwise within 30 minutes.

The separated white, crystalline product was filtered and pre-dried in a nitrogen stream and then finally dried in a vacuum drier at the pressure of 15 mbar and temperature of 100° C. 3.1 g (95%) of the crystalline fumarate (polymorph B) were obtained. Melt. point=216-218° C.

Example 4

Preparation of the Salt of 1-[4-(2-azepan-1-yl-ethoxy)benzyl]-2-(4-hydroxyphenyl)-3-methyl-1H-indol-5-ol with Succinic Acid in the Proportion of 2/1 (bazedoxifene succinate)

The starting compound, benzylated bazedoxifene of formula 7 (2 g; 3.06 mmol) was dissolved in an ethanol/ethyl acetate mixture (95:5) (20 ml) and the catalyst, 2.34%-Pd/C (0.8 g) was added in an inert atmosphere. Then, the reaction mixture was stirred in the hydrogen atmosphere for 5 hours. The catalyst was filtered off through a celite layer in an inert atmosphere. The obtained clear, colourless filtrate was inoculated with bazedoxifene succinate (0.1 g). Then, an ethanolic solution (2 ml) of succinic acid (0.18 g, 1.53 mmol) was added to the solution dropwise within 30 minutes.

The separated white, crystalline product was filtered and dried in a nitrogen stream. 1.46 g (89%) of the crystalline succinate were obtained. Melt point=199-203° C.

Example 5

Preparation of the Salt of 1-[4-(2-azepan-1-yl-ethoxy)benzyl]-2-(4-hydroxyphenyl)-3-methyl-1H-indol-5-ol with Tartaric Acid in the Proportion of 2/1 (bazedoxifene tartrate)

The starting compound, benzylated bazedoxifene of formula 7 (2 g; 3.06 mmol) was dissolved in an ethanol/ethyl acetate mixture (95:5) (20 ml) and the catalyst, 2.34%-Pd/C (0.8 g) was added in an inert atmosphere. Then, the reaction mixture was stirred in the hydrogen atmosphere for 5 hours. The catalyst was filtered off through a celite layer in an inert atmosphere. Then, an ethanolic solution (2 ml) of tartaric acid (0.23 g, 1.53 mmol) was added to the clear filtrate dropwise within 30 minutes.

The separated white, crystalline product was filtered and dried in a nitrogen stream. 1.33 g (80%) of the crystalline tartrate were obtained. Melt point=201-203.8° C.

Example 6

Preparation of the Salt of 1-[4-(2-azepan-1-yl-ethoxy)benzyl]-2-(4-hydroxyphenyl)-3-methyl-1H-indol-5-ol with Oxalic Acid in the Proportion of 2/1 (bazedoxifene oxalate)

The starting compound, benzylated bazedoxifene of formula 7 (1.3 g; 2 mmol) was dissolved in an ethanol/ethyl acetate mixture (95:5) (40 ml) and the catalyst, 2.34%-Pd/C (0.2 g) was added in an inert atmosphere. Then, the reaction mixture was stirred in the hydrogen atmosphere for 5 hours. The catalyst was filtered off through a celite layer in an inert atmosphere. An ethanolic solution (2.5 ml) of oxalic acid dihydrate (0.12 g, 0.95 mmol) was added to the solution dropwise within 30 minutes. A white product started to separate immediately. The separated white, crystalline product was filtered and dried in a nitrogen stream and in a vacuum drier at 50° C. 0.79 g (78%) of the crystalline oxalate were obtained. Melt point=157-165° C.

Example 7

Preparation of the Salt of 1-[4-(2-azepan-1-yl-ethoxy)benzyl]-2-(4-hydroxyphenyl)-3-methyl-1H-indol-5-ol with Citric Acid in the Proportion of 2/1 (bazedoxifene citrate)

The starting compound, benzylated bazedoxifene of formula 7 (1 g; 1.53 mmol) was dissolved in a mixture of toluene/IPA (1:1) (40 ml) and the catalyst, Ra—Ni (0.69 g) was added in an inert atmosphere. Then, the reaction mixture was stirred in the hydrogen atmosphere for 5 hours. The catalyst was filtered off through a celite layer in an inert atmosphere. A solution of citric acid (0.15 g; 0.73 mmol) in 10 ml of the toluene/IPA (1:1) mixture was added to the solution dropwise during 30 minutes.

The separated white product was filtered and dried in a nitrogen stream and in a vacuum drier at 50° C. 0.69 g (73%) of the citrate (2/1) were obtained. Melt. point=120-135° C.

Example 8

Preparation of 1-[4-(2-azepan-1-yl-ethoxy)benzyl]-2-(4-hydroxyphenyl)-3-methyl-1H-indol-5-ol (bazedoxifene)

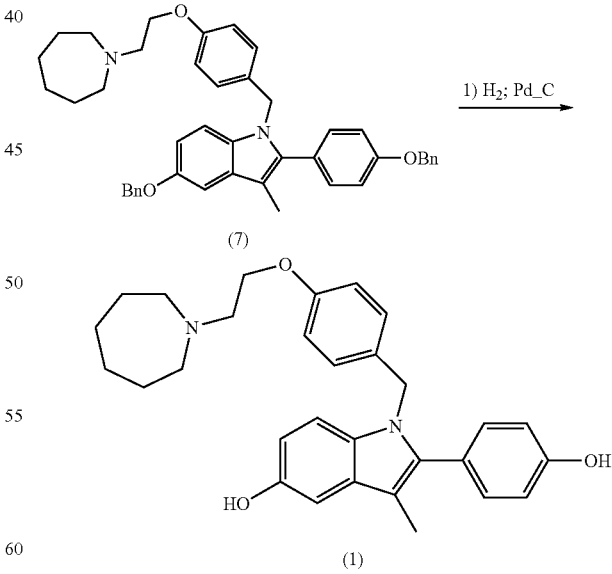

The starting compound, benzylated bazedoxifene of formula 7 (4.8 g; 7.38 mmol) was dissolved in an ethanol/THF mixture (1:1) (80 ml) and the catalyst, 2.34%-Pd/C (0.4 g) was added in an inert atmosphere. Then, the reaction mixture was stirred in the hydrogen atmosphere for 5 hours. The catalyst was filtered off through a celite layer in an inert atmosphere. The obtained clear, colourless filtrate was concentrated until dry.

3.43 g (99%) of the bazedoxifene base were obtained in the form of off-white, solid foam. HPLC content 98.8%.

Example 9

Preparation of the Salt of 1-[4-(2-azepan-1-yl-ethoxy)benzyl]-2-(4-hydroxyphenyl)-3-methyl-1H-indol-5-ol with Formic Acid (bazedoxifene formate)

The starting compound, bazedoxifene base of formula 1 (1 g; 2.13 mmol) was dissolved in a mixture of ethyl acetate (15 ml) and formic acid (2 ml) at 77° C. After cooling to 5° C. a white product slowly separated.

The separated white, crystalline product was filtered and dried in a vacuum drier at 50° C. 0.55 g (50%) of the formate were obtained. Melt. point=206-213° C.

Example 10

Preparation of the Salt of 1-[4-(2-azepan-1-yl-ethoxy)benzyl]-2-(4-hydroxyphenyl)-3-methyl-1H-indol-5-ol with Acetic Acid (bazedoxifene acetate)

The starting compound, benzylated bazedoxifene of formula 7 (3 g; 4.6 mmol) was dissolved in ethyl acetate (30 ml) and the catalyst, 2.34%-Pd/C (0.25 g) was added in an inert atmosphere. Then, the reaction mixture was stirred in the hydrogen atmosphere for 24 hours. The catalyst was filtered off through a celite layer in an inert atmosphere. The obtained clear, colourless filtrate was added to a solution of acetic acid (0.3 ml, 5.1 mmol) in the ethyl acetate (9 ml) and ethanol (2.5) mixture dropwise while being cooled with ice. The separated white substance was filtered and suspended in 30 ml of a mixture of ethyl acetate and ethanol (95:5) and the suspension was refluxed for 5 minutes. After cooling with ice and filtration the product was dried in a vacuum drier at 50° C.

1 g of bazedoxifene acetate was obtained (yield 41%). Melt. point=139-163° C.

The invention claimed is:

1. A salt of 1-[4-(2-azepan-1-yl-ethoxy)benzyl]-2-(4-hydroxyphenyl)-3-methyl-1H-indol-5-ol of formula 1 (bazedoxifene) with a dicarboxylic acid, which acid is a fumaric acid (1)

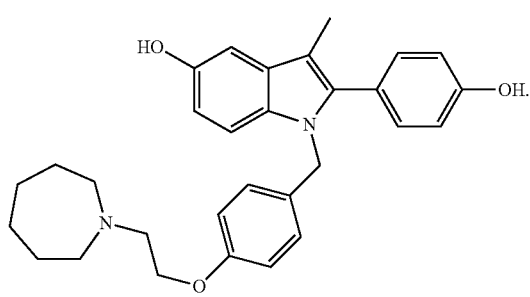

2. The salt according to claim 1, wherein the proportion of bazedoxifene to the fumaric acid is 2:1.

3. The salt according to claim 2, wherein the salt is bazedoxifene fumarate, in a crystalline form.

4. The salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph A, characterized by the following reflections in the X-Ray diffraction pattern: 8.31; 10.38; 12.78; 13.69; 14.72; 21.53; 22.27; 23.24.

5. The salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph A, characterized by the melting point in the temperature interval of 221-224° C.

6. The salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph A, characterized by a maximum at 216° C. in the differential scanning calorimetry.

7. The salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph B, characterized by the following reflections in the X-Ray diffraction pattern: 5.32; 11.93; 12.85; 14.58; 15.87; 18.40; 19.34; 19.73; 20.47; 21.18; 23.63; 24.50.

8. The salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph B, characterized by the melting point in the temperature interval of 216-218° C.

9. The salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph B, characterized by a maximum at 211.4° C. in the differential scanning calorimetry (polymorph B).

10. A mixture of the salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph A, characterized by the following reflections in the X-Ray diffraction pattern: 8.31; 10.38; 12.78; 13.69; 14.72; 21.53; 22.27; 23.24 together with the salt of the 1-[4-(2-azepan-1-yl-ethoxy)benzyl]-2-(4-hydroxyphenyl)-3-methyl-1H-indol-5-ol free base of formula 1 with fumaric acid according to claim 3, which is polymorph B, characterized by the following reflections in the X-Ray diffraction pattern: 5.32; 11.93; 12.85; 14.58; 15.87; 18.40; 19.34; 19.73; 20.47; 21.18; 23.63; 24.50.

11. The salt of the 1-[4-(2-azepan-1-yl-ethoxy)benzyl]-2-(4-hydroxyphenyl)-3-methyl-1H-indol-5-ol free base of formula 1 with acetic acid (bazedoxifene acetate), characterized by the following reflections in the X-Ray diffraction pattern: 13.17; 15.97; 17.95; 19.62; 20.54; 22.08; 25.27.

12. A method of purification of 1-[4-(2-azepan-1-yl-ethoxy)benzyl]-2-(4-hydroxyphenyl)-3-methyl-1H-indol-5-ol, wherein it comprises preparation of a salt of the 1-[4-(2-azepan-1-yl-ethoxy)benzyl]-2-(4-hydroxyphenyl)-3-methyl-1H-indol-5-ol free base of formula 1 with fumaric acid.

13. The method according to claim 12, comprising the preparation of a salt of the 1-[4-(2-azepan-1-yl-ethoxy)benzyl]-2-(4-hydroxyphenyl)-3-methyl-1H-indol-5-ol free base of formula 1 with fumaric acid in the proportion of components 2:1.

14. A pharmaceutical composition comprising a salt according to claim 1.

* * * * *